(12) United States Patent
Ma et al.

(10) Patent No.: US 7,579,014 B2
(45) Date of Patent: Aug. 25, 2009

(54) MESOPOROUS COMPOSITIONS FOR USE IN DRUG DELIVERY

(75) Inventors: Ying Ma, Weatherford, TX (US);
Kenneth J. Balkus, Jr., The Colony, TX (US)

(73) Assignee: Board of Regents the University of Texas System, Austin, TX (US)

( * ) Notice: Subject to any disclaimer, the term of this patent is extended or adjusted under 35 U.S.C. 154(b) by 0 days.

(21) Appl. No.: 11/645,871

(22) Filed: Dec. 27, 2006

(65) Prior Publication Data

US 2007/0104790 A1 May 10, 2007

Related U.S. Application Data

(62) Division of application No. 10/079,443, filed on Feb. 19, 2002, now Pat. No. 7,172,770.

(60) Provisional application No. 60/283,699, filed on Apr. 13, 2001, provisional application No. 60/269,907, filed on Feb. 19, 2001.

(51) Int. Cl.
*A61K 9/10* (2006.01)
*A61K 9/16* (2006.01)
*C01F 7/02* (2006.01)
*C07D 311/72* (2006.01)
*A61P 39/06* (2006.01)
*A61K 47/02* (2006.01)

(52) U.S. Cl. .................. 424/400; 424/484; 424/489; 514/458; 514/769; 423/625; 423/628; 549/408

(58) Field of Classification Search ............... None
See application file for complete search history.

(56) References Cited

U.S. PATENT DOCUMENTS 5,234,695 A * 8/1993 Hobbs et al. ............... 424/489

OTHER PUBLICATIONS

Bagshaw, Stephen A.; Pinnavaia, Thomas J.; Mesoporous Alumina Molecular Sieves; 1996; Angewandte Chemie International Edition English; vol. 35, No. 10; p. 1102-1105.*
Vaudry, Frederic; Khodabadeh, Shervin; Davis, Mark E.; Synthesis of Pure Alumina Mesoporous Materials; 1996; Chemistry of Materials; vol. 8; p. 1451-1464.*

* cited by examiner

*Primary Examiner*—Johann R Richter
*Assistant Examiner*—Christopher R Lea
(74) *Attorney, Agent, or Firm*—Winstead PC

(57) ABSTRACT

The present invention encompasses novel mesoporous compositions comprising vitamin E and alumina, and methods for their synthesis. The mesoporous compositions of the present invention have applications as drug-delivery vehicles.

15 Claims, 6 Drawing Sheets

MESOPOROUS COMPOSITIONS FOR USE IN DRUG DELIVERY

CROSS REFERENCES TO RELATED APPLICATIONS

This application is a divisional of application Ser. No. 10/079,443, filed Feb. 19, 2002 now U.S. Pat. No. 7,172,770, which claims the benefit of U.S. Provisional Application No. 60/269,907, filed Feb. 19, 2001, and U.S. Provisional Application No. 60/283,699, filed Apr. 13, 2001.

BACKGROUND OF THE INVENTION

1. Technical Field of the Invention

The present invention relates to the use of mesoporous compositions for use in drug delivery systems.

2. Description of the Prior Art

Porous substances are generally divided by pore size. For example, those having pore sizes smaller than 2 nm are classified as microporous substances, between 2 and 50 nm are classified as mesoporous substances and larger than 50 nm are classified as macroporous substances. Because of the range of their pore sizes, mesoporous materials are compatible with applications such as separation or sensing of relatively large-organic molecules. Typical of the mesoporous materials are amorphous or polycrystalline solids such as pillared clays and silicates. Unfortunately, the pores in these materials are often irregularly spaced and broadly distributed in size.

There is growing interest in the use of inorganic materials as host matrices for bioactive molecules. The principal advantages of such host/guest type materials include the stability and relative inertness of the materials as well as their easy transportation as free flowing powders. Considerable synthetic effort has therefore been devoted to developing molecular sieve frameworks with pore diameters within the mesoporous range, and the development of a series of molecular sieves having a hexagonal array of uniform mesopores has been reported. A group of researchers at Mobil Oil Corporation have reported a series of mesoporous molecular sieves, named MCM-41, in U.S. Pat. Nos. 5,057,296 and 5,102,643, which are fully incorporated by reference. According to these patents, MCM-41 has a structure exhibiting hexagonal arrangement of straight channels, such as a honeycomb, on a silica plate. MCM-41 is synthesized using the cationic type surfactant, quaternary alkyltrimethylammonium salts $[C_nH_{2n+1}(CH_3)_3N^+X^-]$ and various silica sources, like sodium silicates, tetraethyl orthosilicate, or silica gel, under hydrothermal conditions. On the other hand, the mesoporous materials in the SBA series, another group of synthetic mesoporous materials, are synthesized using neutral templates (Zhao et. al., Science 279, 548 (1998)).

MCM-41 synthesis has been proposed to occur through a liquid crystal templating mechanism. Researchers have proposed that the structure is defined by the organization of surfactant molecules into liquid crystals which serve as templates for the formation of the MCM-41 structure. (Beck et. al., J. Am. Chem. Soc. 114, 10834 (1992), fully incorporated by reference herein). In other words, the first step in the synthesis would correspond to the formation of a micellar rod around the surfactant micelle, which in a second step will produce a hexagonal array of rods, followed by incorporation of an inorganic array (like silica, or silica-alumina) around the rodlike structures. That is, in an aqueous solution, surfactants form a liquid crystal structure which is surrounded by silicate ions and the liquid crystal structure is associated with MCM-41 substance via a hydrothermal reaction and then, removed by calcination at a temperature of 500 to 600° C., to prepare MCM-41.

MCM-41 has been actively researched for characterization and application by many laboratories, because their large and uniform pore sizes allow the entry of otherwise sterically hindered molecules. The pore size of MCM-41 can be adjusted in a range of from 1.6 nm up to 10 nm by modulating the kinds of surfactants or synthesis conditions. Additionally, the easily tailored pore size and availability of compositional variance, provides a versatile range of materials for applications that span from catalysis to drug delivery.

The mesoporous compositions of the present invention are synthesized using a novel templating molecule, vitamin E, which renders the mesoporous compositions of the present invention unique over those described in the art.

A composition comprising vitamin E and silica is taught in U.S. Pat. No. 5,234,695, which is fully incorporated by reference in the disclosure. The invention contemplates the addition of a flow agent to a water dispersible vitamin E composition, where the flow agent is preferably fumed silica having an average particle size of about 0.1 micron. This composition comprises vitamin E and silica and lacks any definite form i.e., represents an amorphous composition.

The composition of the present invention is unique over the amorphous composition described in U.S. Pat. No. 5,234,695, in that said composition is a mesoporous molecular sieve, comprising alumina ($Al_2O_3$) and vitamin E.

Drug insolubility is one of the most challenging issues in the development of many pharmaceutical products. Over one third of the drugs listed in the U.S. Pharmacopoeia and about 50% of new chemical entities are insoluble or poorly soluble in water. As a result, many drugs are marketed as sub-optimal formulations, often giving poor or erratic bioavailability or a greater risk of adverse side effects. Certain aspects of the claimed invention can be used to facilitate the in situ delivery of insoluble or poorly soluble drugs by using a vitamin E TPGS micelle as a host for the delivery of guest molecules.

SUMMARY OF THE INVENTION

It is an object of the present invention to provide novel mesoporous compositions comprising vitamin E and alumina. It is another object of the invention to provide methods for synthesizing said novel mesoporous compositions. It is yet another object of the invention to provide exemplary uses for the mesoporous compositions of the invention.

The mesoporous compositions are synthesized by using Vitamin E d-α-tocopheryl polyethylene glycol 1000 succinate (vitamin E TPGS) as a structure-directing agent. The mesoporous compositions can be synthesized under specific conditions to produce varied morphologies including, but not limited, to gyroids, hexagons, hexagonal rods, discs, and spheres. The synthesis conditions can be modified to control particle morphology, while maintaining the hexagonal mesoporous structure. These new classes of compositions have applications as drug delivery vehicles for vitamin E and other water-insoluble drugs; as a catalyst by fixation of large active complexes in the mesopores; as fiber optic sensors by depositing the mesoporous composition comprising a fluorescent dye at the tip of an optical fiber; and in the preparation of mesoporous membranes for use in separation, fuel cells, and in catalytic membrane reactors.

In accordance with an aspect of the present invention, there is provided a method for preparing a mesoporous composition, comprising the steps of:

(A) dissolving a compound possessing amphipathic properties together with an alumina source in a solvent to form a mixture;
(B) stirring the mixture of step (A);
(C) aging the mixture of step (B) to form a product;
(D) evaporating the product of step (C);
(E) washing, filtering and drying the evaporated product of step (D).

In accordance with another aspect of the present invention, there is provided a mesoporous composition prepared from a mixture comprising vitamin E TPGS and an alumina source.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the invention presented herein.

DETAILED DESCRIPTION OF ILLUSTRATIVE EMBODIMENTS

Figure 1:
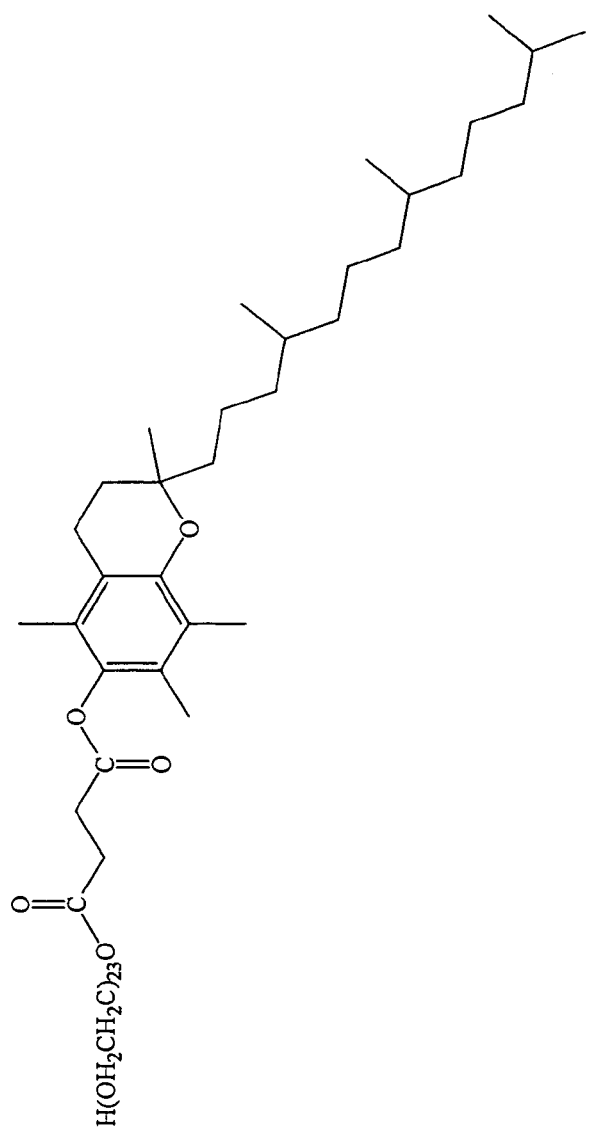
FIG. 1 shows the chemical structure of Vitamin E-TPGS (α-tocopheryl polyethylene glycol 1000 succinate).

The present invention is generally concerned with novel mesoporous compositions, methods for synthesizing these mesoporous compositions and practical applications of the mesoporous compositions. As used herein, the term "mesoporous composition" is synonymous with the term "mesoporous composite". Therefore a silica composite, as used herein, refers to a mesoporous composition comprising silica, and an alumina composite, refers to a mesoporous composition comprising alumina.

The term "mesoporous composition" as-used herein, includes without limitation, those compositions that display pore sizes generally in the range of 2 nm and 50 nm, as well as all compositions produced by the synthesis procedures described herein. In other words, the mesoporous compositions of the present invention are capable of displaying pore sizes that fall outside the 2-50 nm range discussed in the art. The pore sizes can vary depending on the nature of the templating molecule employed in the synthesis of the mesoporous composition of the invention, for example, the length of the polyethylene oxide chains of the templating molecule. The addition of swelling agents to the synthesis mixture can further alter the shape of the micelles, thereby affecting the pore size of the resulting mesoporous composition.

Furthermore, the term "mesoporous composition" as used herein, refers to a composition wherein said composition displays a homogeneity in the pore size i.e., although it is possible to vary pore size between various mesoporous compositions based on the synthesis conditions employed, the pore sizes are homogenous within the context of a specific mesoporous composition.

In accordance with an aspect of the present invention, there is provided a method for preparing a mesoporous composition, comprising the steps of:
(A) dissolving a first compound possessing amphipathic properties together with an alumina source in a first solvent to form a mixture;
(B) stirring the mixture of step (A);
(C) adding a second solvent to the stirred mixture of step (B) accompanied by further stirring;
(D) aging the further stirred mixture of step (C) to form a product;
(E) evaporating the product of step (D); and,
(F) washing, filtering and drying the evaporated product of step (E).

In accordance with another aspect of the present invention, there is provided a mesoporous composition prepared from a mixture comprising vitamin E TPGS and an alumina source and uses for these compositions in drug-delivery systems.

The present invention teaches the synthesis of mesoporous compositions, using biomolecules, as templating agents. It is an object of the present invention to provide a mesoporous composition synthesized with functional templates. The term "functional template" as used herein represents a templating molecule used in the synthesis of the mesoporous compositions of the present invention, which in and of itself has a useful function, preferably a useful bioactive or biological function. The bioactive, functional templating molecules used in the synthesis of the mesoporous compositions of the present invention can be used as drugs or drug delivery vehicles.

By way of example, a functional template contemplated by the present invention is a compound comprising vitamin E. In the present invention, the functional template is preferably an alpha-tocopherol polyethylene glycol ester, and more preferably d-alpha-tocopheryl polyethylene glycol succinate (vitamin E TPGS). Vitamin E TPGS is a water soluble derivative of natural source Vitamin E, and has a dual nature, similar to an amphiphile, of hydrophilicity and lipophilicity. The use of the term vitamin E TPGS as used in the specification and the claims, is intended to encompass the compound having the chemical formula $C_{33}O_5H_{54}(CH_2CH_2O)_n$, where "n" represents the number of polyethylene oxide moieties attached to the acid group of crystalline d-alpha tocopheryl acid succinate. Indeed, the chemical structure of the principal component of a commercial preparation of vitamin E TPGS sold by Eastman Chemicals is represented by $C_{33}O_5H_{54}(CH_2CH_2O)_n$.

The value of "n" in vitamin E TPGS can vary from about 4 to 460, depending on the source of the polyethylene oxide (PEO) moieties used in the preparation of the mesoporous compounds of the present invention. Said sources include, but are not limited to, polyethylene glycol 200 (comprising about 5 PEO moieties), 300 (comprising about 7 PEO moieties), 400 (comprising about 9 PEO moieties), 600 (comprising about 14 PEO moieties), 1000 (comprising about 23 PEO moieties), 6000 (comprising about 136 PEO moieties), 8000 (comprising about 182 PEO moieties), and 20000 (comprising about 455 PEO moieties). By way of example, a form of vitamin E TPGS prepared by esterification of polyethylene glycol 1000 to the acid group of crystalline d-alpha tocopheryl acid succinate, has an "n" value of 23, and is designated as vitamin E TPGS 1000.

Vitamin E TPGS is a surfactant-like amphipathic molecule capable of generating micelles. Amphipathic molecules comprise hydrophilic and hydrophobic surfaces within the same molecule, and therefore readily form micelles. The formation of micelles by vitamin E TPGS enhances its solubility and protects the succinate linkage from hydrolysis in the stomach's acidic environment. Vitamin E TPGS displays distinguishable liquid crystalline phases with increasing water weight percent, and forms hexagonal arrays of micelles at concentrations above its critical micelle concentration of 0.02%.

By using vitamin E TPGS as a template for the synthesis of a mesoporous composition, the present invention-results in the synthesis of a free-flowing powder with improved adsorption efficiencies. As a composition of alumina with vitamin E, the mesoporous composition of the present invention is different from known molecular sieves. As a mesoporous molecular sieve inclusion compound, the mesoporous composition is different from known compositions comprising vitamin E. The use of vitamin E TPGS in the synthesis of the mesoporous compositions of the present invention, is provided for exemplary purposes only, and is not intended to limit the scope of the invention. In other words, all forms of vitamin E, which display the micelle-forming ability of vitamin E TPGS, may be used to generate the mesoporous compositions of the present invention.

Furthermore, the scope of the present invention is not intended to be limited solely to the use of vitamin E as a templating molecule. The method of the present invention may be used to synthesize mesoporous compositions comprising templating molecules including, but not limited to all biological and bioactive molecules that are capable of forming micellar structures. Included within said biological and bioactive molecules are molecules with polyethyleneoxide chains attached for water solubility. Exemplary of such molecules are the drugs ADAGEN®, ONCASPAR®, PROTHECAN®, and PEG-Intron®, manufactured by Enzon, Inc.

In addition, when vitamin E TPGS is used as the templating molecule, the micelles generated by vitamin E TPGS may be used to house drug molecules, specifically water-insoluble dugs. In other words, vitamin E TPGS may serve as a host molecule for the in situ delivery of guest compounds and drugs in physiological systems.

An alumina source is used in the preparation of the mesoporous composition of the present invention. The term "alumina source" as used herein, includes without limitation, compounds that produce aluminum oxide, $Al_2O_3$, when subjected to the steps comprising the method for preparation of the mesoporous composition of the present invention (alumina-producing compounds). The "alumina source" used in the preparation of the mesoporous composition of the present invention preferably includes aluminum tri-sec-butoxide $(C_{12}H_{27}AlO_3)$.

The term "alumina source" further includes without limitation, aluminosilicates i.e., compounds comprising silicon, aluminum and oxygen. The term "alumina source" also includes metalloaluminates, i.e., compounds comprising aluminum, oxygen, and one or more metals. Without limitation, the metals include, zinc, magnesium, sodium, calcium, lithium, strontium, lanthanum and mixtures thereof The "alumina source" used in the preparation of the mesoporous composition of the present invention further includes organoaluminates as well as mixtures of all of the above.

The aging step used in the preparation of the mesoporous composition of the present invention comprises standing the reaction mixture at a specific temperature for a specific length of time i.e., subjecting the mixture to one or more specific time and temperature combinations or "conditions." Said aging step is preferably carried out at 70-95° C. for 2-7 days. The aging step is more preferably carried out at 90° C. over a period of 2 days or 48 hours.

Removal of an excess of the organic templating molecule from the mesoporous composition of the present invention may be accomplished by heating (calcination) or solvent extraction. The process of calcination is preferably carried out at a temperature of 500 to 600° C. The process of calcination is further preferably carried out from between 2 to 15 hours. The process of solvent extraction may be carried out with any solvent, more preferably an organic solvent, and most preferably ethanol. The process of solvent extraction is further preferably carried out between 6 to 18 hours.

The chemicals used in the synthesis of the mesoporous compositions of the present invention include Aluminum-tri-sec-butoxide $(C_{12}H_{27}AlO_3;$ Aldrich); sec-butanol $(CH_3CHOHCH_2CH_3;$ Aldrich); Absolute ethanol $(CH_3CH_2OH);$ Aldrich); Vitamin E TPGS $(C_{33}O_5H_{54}(CH_2CH_2O)_n;$ Eastman Chemicals). Simulated gastric fluid was prepared in order to mimic conditions in the stomach so as to ascertain the drug-delivery capabilities of the mesoporous compositions of the present invention. Simulated gastric fluid was prepared as follows: 2 g of NaCl was dissolved into 750 ml of deionized water along with 3.2 g of pepsin, a protease. 7 ml of concentrated HCl was then added, and finally water was added to the volume of 1000 ml. However, because pepsin absorbs in the same region of the UV-Vis spectrum as Vitamin E-TPGS, Vitamin E-TPGS was excluded from the simulated gastric fluid preparation.

Mesoporous compositions comprising vitamin E TPGS and silica can be prepared under acidic conditions. Preparation of an alumina version of the mesoporous composition of the claimed invention presents a challenge because $Al_2O_3$ is amphiphilic and is chemically much less stable than $SiO_2$, which therefore requires more strictly controlled synthesis conditions. In general, the conditions and procedures for making a silica-comprising mesoporous composition do not work for the preparation of an alumina-comprising composition. Likewise, procedures described in the literature for making mesoporous $Al_2O_3$ also did not work. For example, a recipe for making mesoporous $Al_2O_3$ using formamide as a solvent and sodium dodecylbenzensulfonate as a surfactant produced only a viscous brown gel with Vitamin E. Furthermore, the addition of Vitamin E-TPGS to a partially hydrolyzed aluminum tri-sec-butoxide suspension in alcohol (ethanol or 2-propanol) leads to a completely amorphous gel that is sticky and difficult to isolate. For those conditions reported for making mesoporous $Al_2O_3$ molecular sieves using neutral polyether templates, poorly ordered materials are obtained that are not stable to calcination. These materials are also brittle and hard to grind. After a rigorous course of experimentation, a set of conditions has been obtained that leads to stable alumina composites comprising vitamin E TPGS. The key step was the additional solvent evaporation step following aging for the filtered gelatinous products, instead of the drying process used with silica-based mesoporous compositions.

Table 1 lists the gel composition and aging conditions for a series of mesoporous compositions comprising alumina.

TABLE 1

Sample nomenclatures and synthesis conditions for selected mesoporous compositions comprising alumina

| Sample* | Batch Composition** | Aging Time (days) | As Synthesized Products | Calcined Products |
|---|---|---|---|---|
| Al-B-2-95 | 100:1:300:35 | 2 | *** | 77 Å |
| Al-B-3-95 | 100:2:300:35 | 2 | 85 Å**** | 84 Å |

TABLE 1-continued

Sample nomenclatures and synthesis conditions for selected
mesoporous compositions comprising alumina

| Sample* | Batch Composition** | Aging Time (days) | As Synthesized Products | Calcined Products |
|---|---|---|---|---|
| Al-B-4-95 | 100:2:300:70 | 4 | 86 Å | 82 Å |
| Al-B-5-95 | 100:2.5:300:35 | 2 | *** | 85 Å |
| Al-B-2-75 | 100:1:300:35 | 7 | *** | 74 Å |
| Al-B-3-75 | 100:2:300:35 | 7 | *** | 81 Å |
| Al-E-2-75 | 100:1:300:35 | 7 | *** | 86 Å |
| Al-E-3-75 | 100:2:300:35 | 7 | *** | 86 Å |
| Al-E-4-75 | 100:1.5:300:35 | 6 | *** | 80 Å |

*The letter following Al refers to the organic solvent used, B represents sec-butanol and E represents ethanol; the following number is the label of the sample within the same series; the last two-digit number is the aging temperature.
**Batch composition refers to the ratio of Al tri-sec-butoxide (mmol): Vitamin E-TPGS (mmol): H$_2$O (mmol): organic solvent (ml).
***X-ray diffraction pattern not well defined.
****'d' spacing of the low angle diffraction peak.

In accordance with an aspect of the present invention, there is provided a method for preparing a mesoporous composition, comprising the steps of:
(A) dissolving a first compound possessing amphipathic properties together with an alumina source in a first solvent to form a mixture;
(B) stirring the mixture of step (A);
(C) adding a second solvent to the stirred mixture of step (B) accompanied by further stirring;
(D) aging the further stirred mixture of step (C) to form a product;
(E) evaporating the product of step (D); and,
(F) washing, filtering and drying the evaporated product of step (E).

Figure 2:
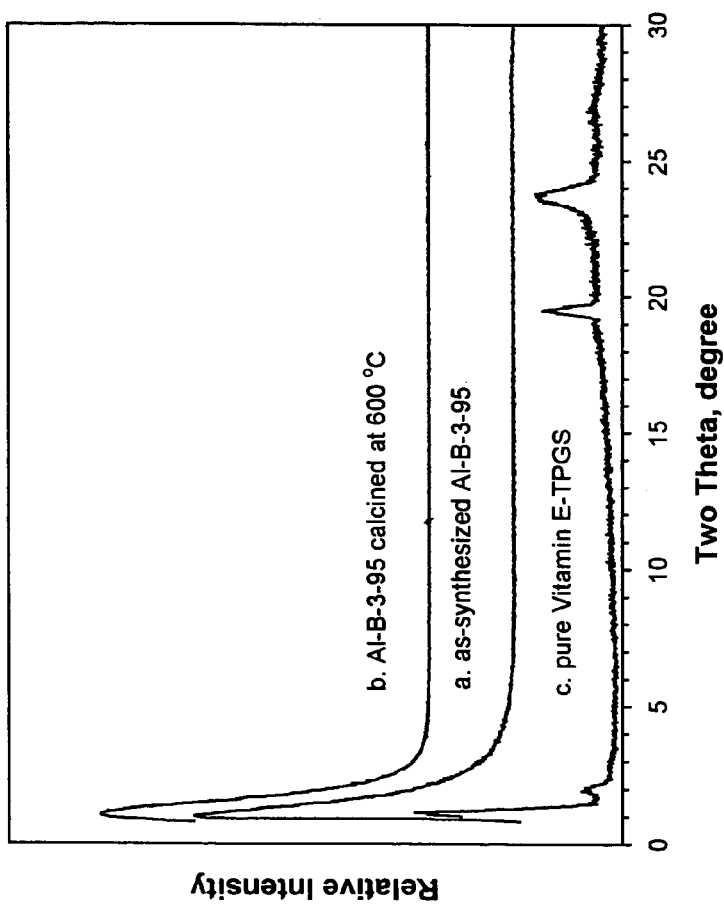
FIG. 2 shows the powder X-ray diffraction patterns of (a) As-synthesized Al-B-3-95; (b) Al-B-3-95 calcined at 600° C.; and (c) Pure Vitamin E TPGS.

The compound in step (A) possessing amphipathic properties is preferably Vitamin E-TPGS. The alumina source used in step (A) is preferably Al tri-sec-butoxide and solvent in step (A) is preferably either sec-butanol, ethanol or water. The as-formed fluid gel mixture of step (B) is allowed to age at an elevated temperature (70-95° C.) for 2-7 days without decanting the supernatant to promote hydrolysis, following which the solvent is evaporated at the same temperature or higher for 2 days to promote condensation. Light-colored free flowing powders are obtained, which are soft and easy to grind. X-ray diffraction patterns show a broad, intense peak around 80 Å for as-synthesized Al-B-3-95. The X-ray diffraction pattern of pure Vitamin E-TPGS plotted as FIG. 2(c) for comparison. It is noteworthy that none of the diffraction peaks for vitamin E-TPGS are observed in unwashed samples. This suggests that all Vitamin E-TPGS in the batch is successfully encapsulated instead of adsorbing onto the surface.

Figure 3:
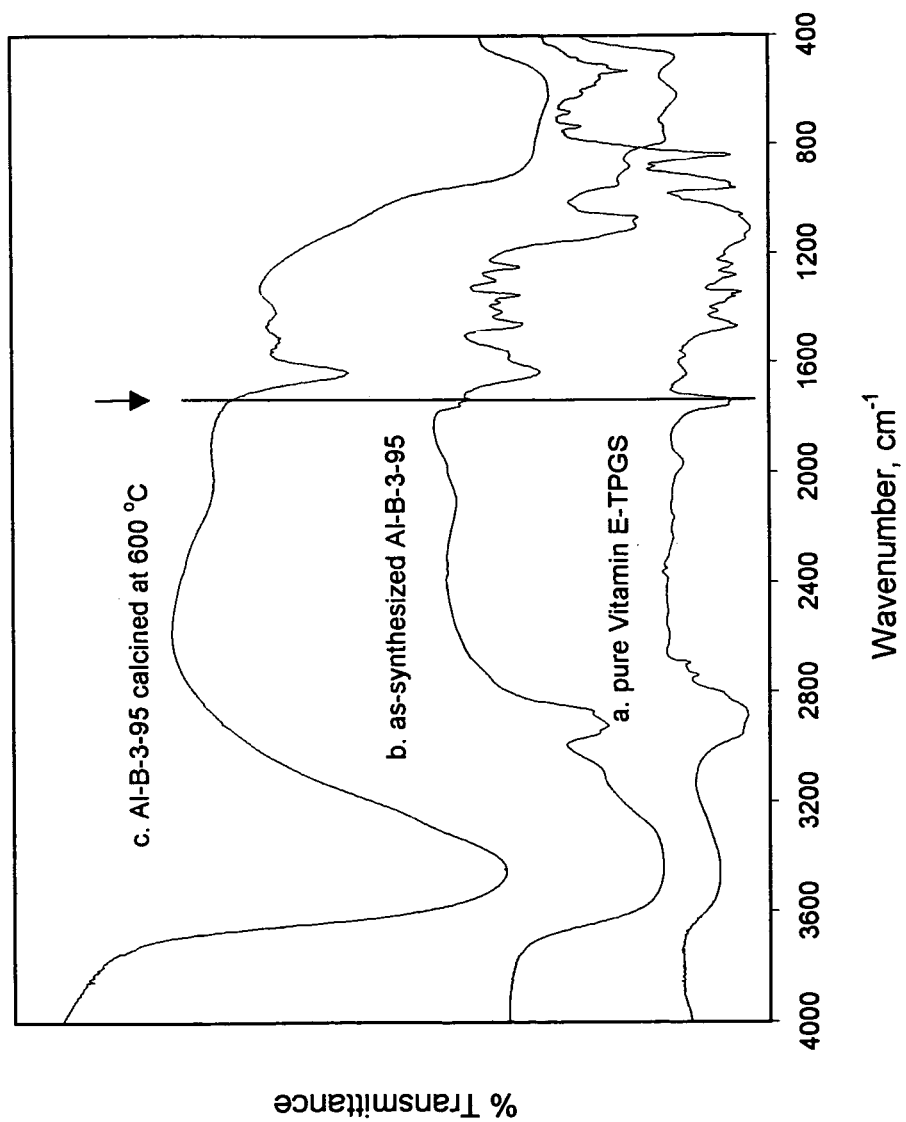
FIG. 3 shows the FTIR (Fourier Transform Infrared Spectroscopy) spectra of (a) Pure Vitamin E TPGS; (b) As-synthesized Al-B-3-95 and (c) Al-B-3-95 calcined at 600° C.

FTIR spectra of the as-synthesized Al-B-3-95 reveals more evidence for template inclusion (FIGS. 3(a)-(c)). FIG. 3a demonstrates the characteristic IR vibrations of a pure Vitamin E-TPGS. The peak at 1741 cm$^{-1}$ is characteristic of the carbonyl group associated with the succinate linkage, and indicates the intact of the Vitamin E-TPGS micellar structure during the synthesis process (FIG. 3(b)). After this sample is calcined at 600° C. for several hours where all of the Vitamin E-TPGS is burnt off, the peak at 1741 cm$^{-1}$ disappeared (FIG. 3(c)).

An objective of the invention is to overcome the difficulty of handling and delivery of Vitamin E-TPGS, which has a sticky texture, and to synthesize the composite material as free flowing powders. To achieve such a composite, the pH of the reaction mixture, the Vitamin E-TPGS to Al ratio, the water to Al ratio, the aging temperature, and the evaporation temperature were varied to optimize the synthesis.

The synthesis is very sensitive to the pH of the reaction mixtures. As mentioned previously, an acidic media (pH 1) which led to the formation of free flowing powders of all silica composites, left these reaction mixtures as transparent sols. In addition, the formamide/HCl mixed media (pH=2-3), which has been used to shape the mesoporous silica, does not work for the alumina system. Even with a much weaker acid, acetic acid, the reaction system remained a clear solution. Also, slightly basic media (pH 8-9) led to an amorphous Al$_2$O$_3$ precipitate immediately. Thus the synthesis conducted in a neutral environment is preferable in producing Vitamin E-TPGS encapsulated free flowing powders when using alumina.

Synthesis conducted in an ethanol media produces free flowing powders as in the case of sec-butanol media, although the maximum aging temperature for an ethanol batch is limited to 78° C., its boiling point (bp), to avoid autogeneous pressure, which is unfavorable for the formation of free flowing powders. With a boiling point of 98° C., a sec-butanol batch can be aged at 95° C., shortening the aging time from a 7 day synthesis in ethanol to a 2 day period in sec-butanol.

The amount of water is also very critical to the synthesis. The free flowing powders are easily obtained with a molar ratio of H$_2$O to Al equal to 2-3. When the amount of H$_2$O is in large excess, the products are hard gels. Peptization of alumina gel with nitric acid (HNO$_3$) led to the formation of Al$_2$O$_3$ ceramic eventually, although it is not a choice in this research, as acid destroys the host/guest composite structures.

The molar ratio of Vitamin E-TPGS to Al in the mesoporous composition of the invention can range from 0:100 to 2.5:100 in this reaction system (see Al-B-5-95 in Table 1). This means that as much as 0.75 g of Vitamin E-TPGS can be encapsulated into one gram of Al$_2$O$_3$. The measurement of the weight difference before and after the calcinations at 600° C. confirm the amount of encapsulated Vitamin E-TPGS. The large loading of Vitamin E-TPGS into the mesoporous composition of the present invention provides an advantage in being able to control the composition of said mesoporous composition.

Figure 4A:
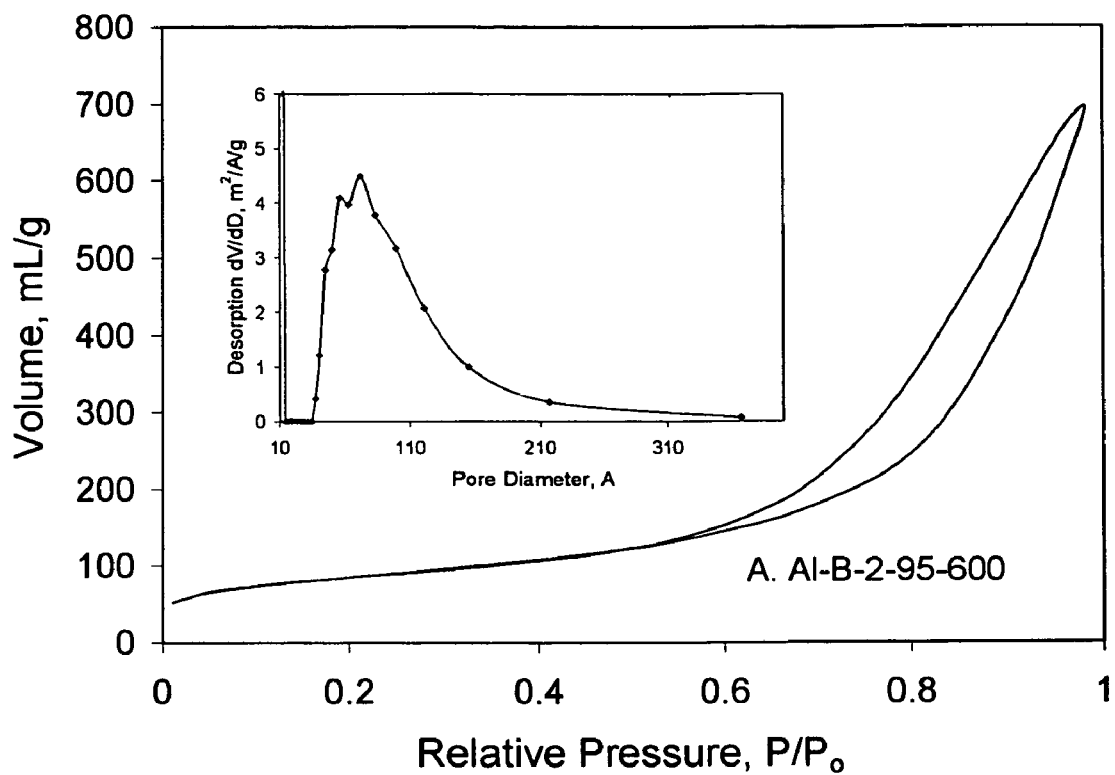
FIGS. 4A-4C show the isotherm and pore distributions of (A) Al-B-2-95-600; (B) Al-B-3-95-600; and (C) Al-E-4-75-500.
Figure 4B:
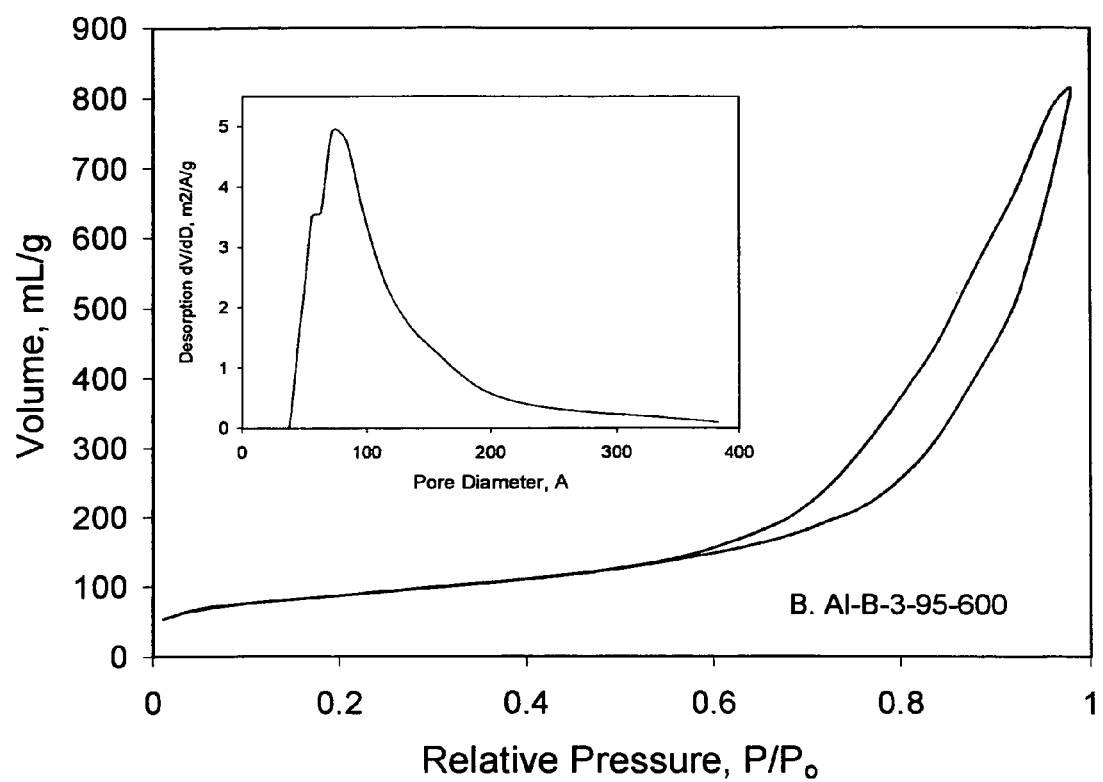
Figure 4C:
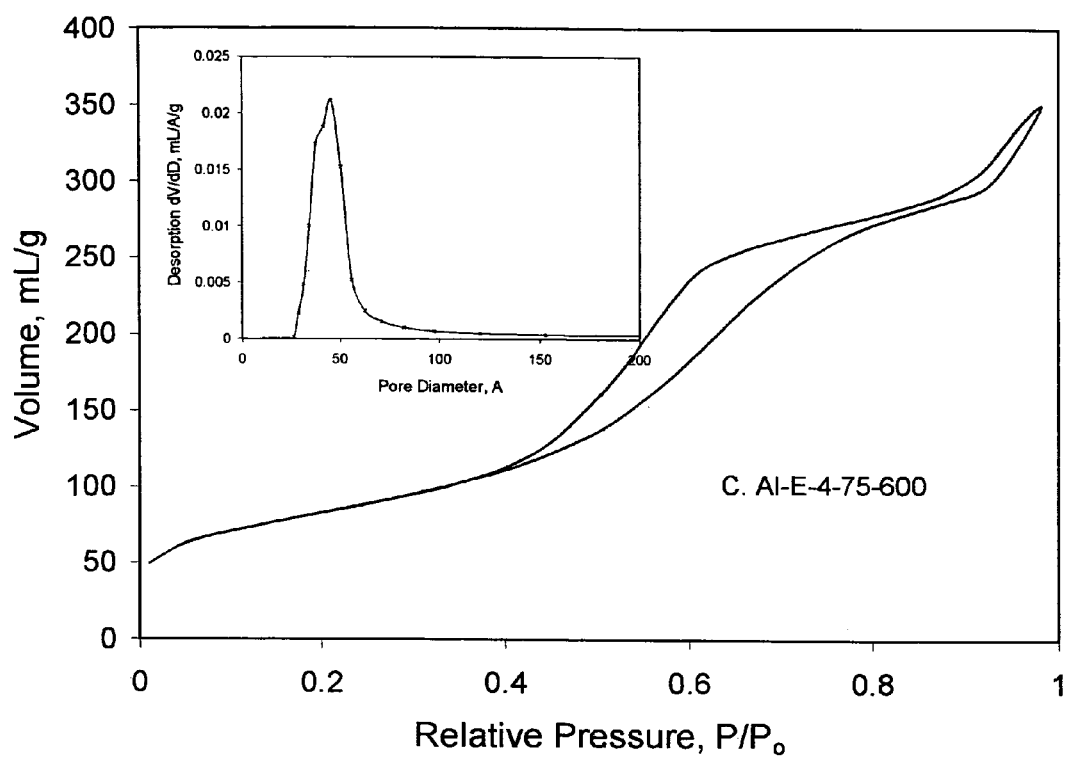

BET surface area measurements show that the calcined materials are porous (all around 300 m$^2$/g). N$_2$ isotherm show that in samples Al-B-2-95-600 and Al-B-3-95-600, the hysteresis loops started at P/P$_o$=0.6 and closed at P/P$_o$=1 (FIGS. 4A and 4B), while sample Al-E-2-75-500 has two hysteresis loops. The first loop ends before P/P$_o$=0.8, followed by a much smaller loop starting after P/P$_o$=0.85 (FIG. 4C). A hysteresis loop after P/P$_o$=0.8 indicates the existence of interparticle pores or textual pores. However, it is clear that with a lower calcination temperature, the amount of these textual pores is largely decreased. All calcined samples demonstrate pores only in the range of 40-200 Å. Among the three samples measured, namely, Al-E-2-75-500, Al-B-2-05-800, and Al-B-3-95-600, Al-E-2-75-500 shows the narrowest pore size distribution around 52 Å and a PSD range from 40-100 Å, which corresponds to the loop below P/P$_o$=0.8, resulting from the condensation of the adsorption within the framework-confined mesopores. With the calcination temperature increased to 600° C., the averaged pore sizes moved to 71 Å with a much broader PSD (50-200 Å). It is known that Vitamin E-TPGS forms hexagonal and lamellar phases in aqueous solutions. This has been observed in all mesoporous composition materials comprising silica. In the case of mesoporous compositions comprising alumina, preliminary transmission electron micrograph (TEM) results on the as-synthesized alumina composite samples revealed a wormhole structure. X-ray diffraction patterns of a calcined sample exhibit a very intense peak at 70, 77, and 84 Å, respectively, for Al-E-2-75-500, Al-B-2-05-800, and Al-B-3-95-600. The 'd' spacing and peak width increase in the same order as the pore size and pore size distribution (PSD), indicating a good match between the X-ray diffraction patterns and the pore structures in the calcined alumina composite materials. This suggests that the mesostructure of the $Al_2O_3$ host was largely preserved after calcination and indicates that these materials are stable to at least 600° C. A molar ratio of Al to water of 1:3 and a Vitamin E-TPGS:Al molar ratio in the as-synthesized samples of 1-2.5:100, resulted in well-defined diffraction peaks.

WORKING EXAMPLES

It is believed that all of the attributes of the present invention can be seen in the following examples, which are intended to illustrate, but not limit the scope of the invention.

Synthesis of Mesoporous Composition Comprising Alumina

A typical synthesis for a mesoporous composition was conducted as follows: a mixture of 0.30 to 0.90 grams of Vitamin E-TPGS and 4.93 grams of aluminum tri-sec-butoxide was dissolved into 25 ml of sec-butanol. The solution was stirred for 3 to 4 hours at room temperature (i.e., about 25-30° C.). A mixture of 1.08 g of water and 10 ml of sec-butanol, well mixed beforehand, was then added dropwise into the above solution. The resultant gel having a molar ratio of $Al_2O_3$:Vitamin E:$H_2O$:sec-BuOH 100:1-3:300:270 was continuously stirred for another 12 hours at room temperature (i.e., about 25-30° C.). The reaction mixture was then capped in a polypropylene bottle and placed into a 90° C. oven aging for 2 days, after which the cap was removed to let sec-butanol evaporate for 10 hours at 90° C. The resultant white or light yellow powders were washed with deionized water and then ethanol by centrifugation, collected by filtration, and dried at room temperature (i.e., about 25-30° C.).

Drug Delivery using a Mesoporous Composition Comprising Alumina

A principle advantage of bio composite materials is the stability and relative inertness of the composites during transportation. To evaluate this property in the mesoporous composition of the present invention, the as-synthesized Al-B-3-95 was allowed to stir in water at pH 7 for 6 hours. Less than 2% of the encapsulated vitamin E TPGS was released into water during the 6-hour stirring period. This demonstrates that the composition of this bio composite material is very stable when delivered at neutral pH.

To achieve the goal of drug delivery, Vitamin E-TPGS needs to be released as a micelle from the composite after being delivered. As-synthesized Al-B-2-95 and Al-B-3-95 were placed in a simulated gastric fluid (SGF; U.S. Pharmacoepia, Vol. 19, p. 765 (1975)) at pH 1.2, and stirred for 30 min, the normal duration of food in stomach. A UV-Vis analysis of the SGF revealed 93% and 85% recovery of Vitamin E-TPGS respectively. Thus, the alumina composition dissolved in pH 1.2 to release the intact micelle. This can be compared with silica compositions that do not dissolve and release the vitamin E micelles. Although the vitamin E itself is an important biomolecule, the micelle is also capable of encapsulating other lipophilic and/or pH sensitive drugs.

The invention claimed is:

1. A mixture for the preparation of a mesoporous composition, the mixture comprising an alpha tocopherol polyethylene glycol ester and an alumina source.

2. The mixture of claim 1, wherein the alpha tocopherol polyethylene glycol ester is vitamin E TPGS.

3. The mixture of claim 2, wherein the alumina source is Aluminum-tri-sec-butoxide.

4. The mixture of claim 3, comprising alumina, vitamin E TPGS, water and sec-butanol in the ratio 100:1-3:300:270 respectively.

5. The mixture of claim 3, comprising alumina, vitamin E TPGS, water and sec-butanol in the ratio 100:1:200:35 respectively.

6. The mixture of claim 3, comprising alumina, vitamin E TPGS, water and sec-butanol in the ratio 100:1:300:35 respectively.

7. The mixture of claim 3, comprising alumina, vitamin E TPGS, water and sec-butanol in the ratio 100:2:300:35 respectively.

8. The mixture of claim 3, comprising alumina, vitamin E TPGS, water and sec-butanol in the ratio 100:1:300:70 respectively.

9. The mixture of claim 3, comprising alumina, vitamin E TPGS, water and sec-butanol in the ratio 100:2.5:300:35 respectively.

10. The mixture of claim 3, comprising alumina, vitamin E TPGS, water and sec-butanol in the ratio 100:3:300:35 respectively.

11. A mixture for the preparation of a mesoporous composition comprising a compound having the formula $C_{33}O_5H_{54}(CH_2CH_2O)_{23}$, ethanol, water and an alumina source.

12. The mixture of claim 11 wherein the ratio of alumina, $C_{33}O_5H_{54}(CH_2CH_2O)_{23}$, water and ethanol is 100:1:200:35.

13. The mixture of claim 11 wherein the ratio of alumina, $C_{33}O_5H_{54}(CH_2CH_2O)_{23}$, water and ethanol is 100:1:300:35.

14. The mixture of claim 11 wherein the ratio of alumina, $C_{33}O_5H_{54}(CH_2CH_2O)_{23}$, water and ethanol is 100:2:300:35.

15. The mixture of claim 11 wherein the ratio of alumina, $C_{33}O_5H_{54}(CH_2CH_2O)_{23}$, water and ethanol is 100:1.5:300:35.

* * * * *